United States Patent
Shears et al.

(10) Patent No.: US 9,943,656 B2
(45) Date of Patent: Apr. 17, 2018

(54) METERED-DOSE INHALER COUNTER WITH SWITCH AND METERED-DOSE INHALER INCLUDING SUCH A COUNTER

(71) Applicants: PRESSPART GMBH & CO. KG, Marsberg (DE); Dana Shears, Cary, NC (US); Kevin Ferenc, Sun Prarie, WI (US); Greg Falendysz, Sun Prarie, WI (US); Steve Cantley, Madison, WI (US)

(72) Inventors: Dana Shears, Cary, NC (US); Kevin Ferenc, Sun Prarie, WI (US); Greg Falendysz, Sun Prarie, WI (US); Steve Cantley, Madison, WI (US); Michael Denzin, Lake Mills, WI (US)

(73) Assignee: Presspart GmbH & Co. KG, Marsberg (DE)

( * ) Notice: Subject to any disclaimer, the term of this patent is extended or adjusted under 35 U.S.C. 154(b) by 0 days.

(21) Appl. No.: 15/311,098

(22) PCT Filed: Aug. 26, 2015

(86) PCT No.: PCT/IB2015/056477
§ 371 (c)(1),
(2) Date: Nov. 14, 2016

(87) PCT Pub. No.: WO2016/030844
PCT Pub. Date: Mar. 3, 2016

(65) Prior Publication Data
US 2017/0087312 A1     Mar. 30, 2017

Related U.S. Application Data

(60) Provisional application No. 62/042,437, filed on Aug. 27, 2014.

(51) Int. Cl.
*A61M 15/00*     (2006.01)

(52) U.S. Cl.
CPC ........ *A61M 15/008* (2014.02); *A61M 15/009* (2013.01); *A61M 15/0083* (2014.02);
(Continued)

(58) Field of Classification Search
CPC ............ A61M 15/0068; A61M 15/007; A61M 15/0071; A61M 15/008; A61M 15/0083; A61M 15/009; A61M 2205/502
See application file for complete search history.

(56) References Cited

U.S. PATENT DOCUMENTS 6,285,731 B1 * 9/2001 Marnfeldt ......... A61M 15/0065
                                              128/200.14
2004/0255936 A1  12/2004 Urbanus
(Continued)

FOREIGN PATENT DOCUMENTS

| GB | 2470188 | 11/2010 |
|----|---------|---------|
| WO | WO 95/07724 | 3/1995 |
| WO | WO 2007/031325 | 3/2007 |

OTHER PUBLICATIONS

International Search Report and Written Opinion for PCT/IB2015/056477 dated Nov. 5, 2015, 7 pages.
(Continued)

*Primary Examiner* — Justine Yu
*Assistant Examiner* — Timothy Stanis
(74) *Attorney, Agent, or Firm* — Myers Bigel, P.A.

(57) ABSTRACT

A dose counter includes a triggering unit having at least a first and a second trigger member thereon. The triggering unit is configured interact with the canister of a metered-dose inhaler when the canister moves in a longitudinal direction from a rest position to an activation position. A circuit assembly includes a substrate with at least a first and
(Continued)

a second switch thereon. The first and second switches are configured to interact with the first and second trigger members when the canister moves from the rest position to the activation position. The circuit assembly includes a counting circuit that is configured to receive a signal from the first and second switches and to determine when the metered dose inhaler is activated.

22 Claims, 10 Drawing Sheets

(52) U.S. Cl.
CPC ....... *A61M 15/007* (2014.02); *A61M 15/0071* (2014.02); *A61M 2205/502* (2013.01)

(56) References Cited

U.S. PATENT DOCUMENTS

| | | | |
|---|---|---|---|
| 2005/0028815 A1* | 2/2005 | Deaton | A61M 15/0065 128/200.23 |
| 2005/0076904 A1* | 4/2005 | Jones | A61M 15/009 128/200.23 |

OTHER PUBLICATIONS

International Preliminary Report on Patentability for PCT/IB2015/056477 dated Sep. 1, 2016, 16 pages.

\* cited by examiner

METERED-DOSE INHALER COUNTER WITH SWITCH AND METERED-DOSE INHALER INCLUDING SUCH A COUNTER

CROSS-REFERENCE TO RELATED APPLICATION

This application is a 35 U.S.C. § 371 national stage application of PCT International Application No. PCT/IB2015/056477, filed on 26 Aug. 2015, which claims the benefit of U.S. Provisional Patent Application No. 62/042,437 filed 27 Aug. 2014, the disclosures and contents of which are incorporated by reference herein in their entireties.

FIELD OF THE INVENTION

The present invention relates to a metered-dose inhaler counter, to metered dose inhalers including the metered dose inhaler counter, and to related methods.

BACKGROUND

Metered-dose inhalers (MDIs) are medication delivery devices that deliver a pharmaceutical formulation including one or more pharmaceutically active compounds ("active ingredients") to a human or other mammalian patient.

Typically the pharmaceutical formulation is delivered by the MDI as unit doses in the form of an aerosol. Each actuation of the MDI delivers one unit dose. The unit dose is expelled by the MDI and is taken into the body of the patient on inhalation, via the nose or mouth. The pharmaceutical formulation is delivered to or via the respiratory tract, notably to the lungs, of the patient on inhalation.

The MDI includes a metering valve which is configured to ensure that each dose of the pharmaceutical formulation expelled by the MDI is the same, within permitted tolerances. In particular, each dose should include the same amount of the active ingredient(s). Generally, the metering valve is configured to dispense a constant volume of the pharmaceutical formulation on each actuation of the MDI.

Although efforts have been made to provide mechanical dose counters, these dose counters may add significant cost and materials to the device and may be inaccurate. Mechanical dose counters may not be able to differentiate events when a dose is actually delivered as compared with other events, such as when a metered-dose inhaler is dropped on the ground or otherwise experiences movement that does not press the metering valve sufficiently for a dose to be delivered. Hence mechanical dose counters have not gained widespread acceptance from healthcare providers. Electromechanical and electronic dose counters have also been proposed but have yet to achieve a sufficiently low cost and sufficiently high reliability.

SUMMARY OF EMBODIMENTS OF THE INVENTION

In some embodiments, a dose counter for a metered dose inhaler is provided. The metered dose inhaler has an actuation housing and canister with an activation valve at a valve end of the canister. The canister is configured to be received in the actuation housing and to move from a rest position to an activation position in which the valve is depressed against a bottom portion of the actuation housing. The dose counter includes a triggering unit having at least a first and a second trigger member thereon. The triggering unit is configured to interact with the canister when the canister moves in a longitudinal direction from the rest position to the activation position. A circuit assembly includes a substrate with at least a first and a second switch thereon. The first and second switches are configured to interact with the first and second trigger members when the canister moves from the rest position to the activation position such that the first trigger member triggers the first switch when the canister reaches a first longitudinal position and the second trigger member triggers the second switch when the canister reaches a second longitudinal position that is different from the first longitudinal position during movement of the canister from the rest position to the activation position. The circuit assembly includes a counting circuit that is configured to receive a signal from the first and second switches indicating at least a first time when the first switch is triggered by the first trigger member and a second time when the second switch is triggered by the second trigger member, and to determine when the metered dose inhaler is activated responsive to the first and second time.

In some embodiments, the first and second trigger members are configured to move from a first position to a second position to activate the first and second switches when the canister moves in the longitudinal direction. The triggering unit may include first and second finger members that are operatively connected to the first and second trigger members, respectively, wherein the first finger member is configured to move the first trigger member in a lateral direction when the canister reaches the first longitudinal position and the second finger member is configured to move the second trigger member in the lateral direction when the canister reaches the second longitudinal position.

In some embodiments, the second longitudinal position of the canister is a position in which the valve is depressed against the bottom portion of the actuation housing.

In some embodiments, the counting circuit is configured to determine whether the metered dose inhaler is activated when a time difference between the first and second time is less than a threshold amount.

In some embodiments, the triggering unit comprises a body portion that is configured to be positioned in the actuation housing between a wall of the actuation housing and the canister. When the triggering unit is positioned in the actuation housing between the wall of the actuation housing and the canister, the first and second finger members may extend in a direction toward the canister in the first position and move in a lateral direction toward the wall of the actuation housing in the second position. The first and second finger members of the triggering unit may be biased to the first position when the canister is in the rest position. The circuit assembly may be configured to be positioned between the triggering unit body portion and the wall of the actuation housing. The first and second switches may be on a first side of the circuit assembly substrate, and the circuit assembly may further include a display on a second, opposite side of the circuit assembly substrate. When the counting circuit determines when the metered dose inhaler is activated responsive to the first and second time, the counting circuit may increment a counting indicia and display the counting indicia on the display. The display may be an electronic ink display. The triggering unit body portion may have a first end and an opposite second end, and the finger members may be on the first end. The triggering unit may include an overhanging member that defines a recessed opening that is configured to receive the counting circuit assembly therein. The overhanging member may include a display opening for receiving the display therein so that the display is visible to a user.

In some embodiments, the counting circuit is positioned on the substrate of the circuit assembly.

In some embodiments, a metered-dose inhaler assembly is provided. The metered-dose inhaler assembly includes a metered dose inhaler having an actuation housing and canister with an activation valve at a valve end of the canister. The canister is configured to be received in the actuation housing and to move from a rest position to an activation position in which the valve is depressed against a bottom portion of the actuation housing. A dose counter in the actuation housing includes a triggering unit having at least a first and a second trigger member thereon. The triggering unit is configured interact with the canister when the canister moves in a longitudinal direction from the rest position to the activation position. A circuit assembly includes a substrate with at least a first and a second switch thereon. The first and second switches are configured to interact with the first and second trigger members when the canister moves from the rest position to the activation position such that the first trigger member triggers the first switch when the canister reaches a first longitudinal position and the second trigger member triggers the second switch when the canister reaches a second longitudinal position that is different from the first longitudinal position during movement of the canister from the rest position to the activation position. The circuit assembly includes a counting circuit that is configured to receive a signal from the first and second switches indicating at least a first time when the first switch is triggered by the first trigger member and a second time when the second switch is triggered by the second trigger member, and to determine when the metered dose inhaler is activated responsive to the first and second time.

In some embodiments, the first and second trigger members are configured to move from a first position to a second position to activate the first and second switches when the canister moves in the longitudinal direction. The triggering unit may include first and second finger members that are operatively connected to the first and second trigger members, respectively, wherein the first finger member is configured to move the first trigger member in a lateral direction when the canister reaches the first longitudinal position and the second finger member is configured to move the second trigger member in the lateral direction when the canister reaches the second longitudinal position.

In some embodiments, the second longitudinal position of the canister is a position in which the valve is depressed against the bottom portion of the actuation housing.

In some embodiments, the counting circuit is configured to determine whether the metered dose inhaler is activated when a time difference between the first and second time is less than a threshold amount.

In some embodiments, the triggering unit comprises a body portion that is configured to be positioned in the actuation housing between a wall of the actuation housing and the canister. When the triggering unit is positioned in the actuation housing between the wall of the actuation housing and the canister, the first and second finger members may extend in a direction toward the canister in the first position and move in a lateral direction toward the wall of the actuation housing in the second position. The first and second finger members of the triggering unit may be biased to the first position when the canister is in the rest position. The circuit assembly may be configured to be positioned between the triggering unit body portion and the wall of the actuation housing. The first and second switches may be on a first side of the circuit assembly substrate, and the circuit assembly may further include a display on a second, opposite side of the circuit assembly substrate. When the counting circuit determines when the metered dose inhaler is activated responsive to the first and second time, the counting circuit may increment a counting indicia and display the counting indicia on the display. The display may be an electronic ink display. The triggering unit body portion may have a first end and an opposite second end, and the finger members may be on the first end. The triggering unit may include an overhanging member that defines a recessed opening that is configured to receive the counting circuit assembly therein. The overhanging member may include a display opening for receiving the display therein so that the display is visible to a user.

In some embodiments, the counting circuit is positioned on the substrate of the circuit assembly.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF EMBODIMENTS OF THE INVENTION

Figure 1:
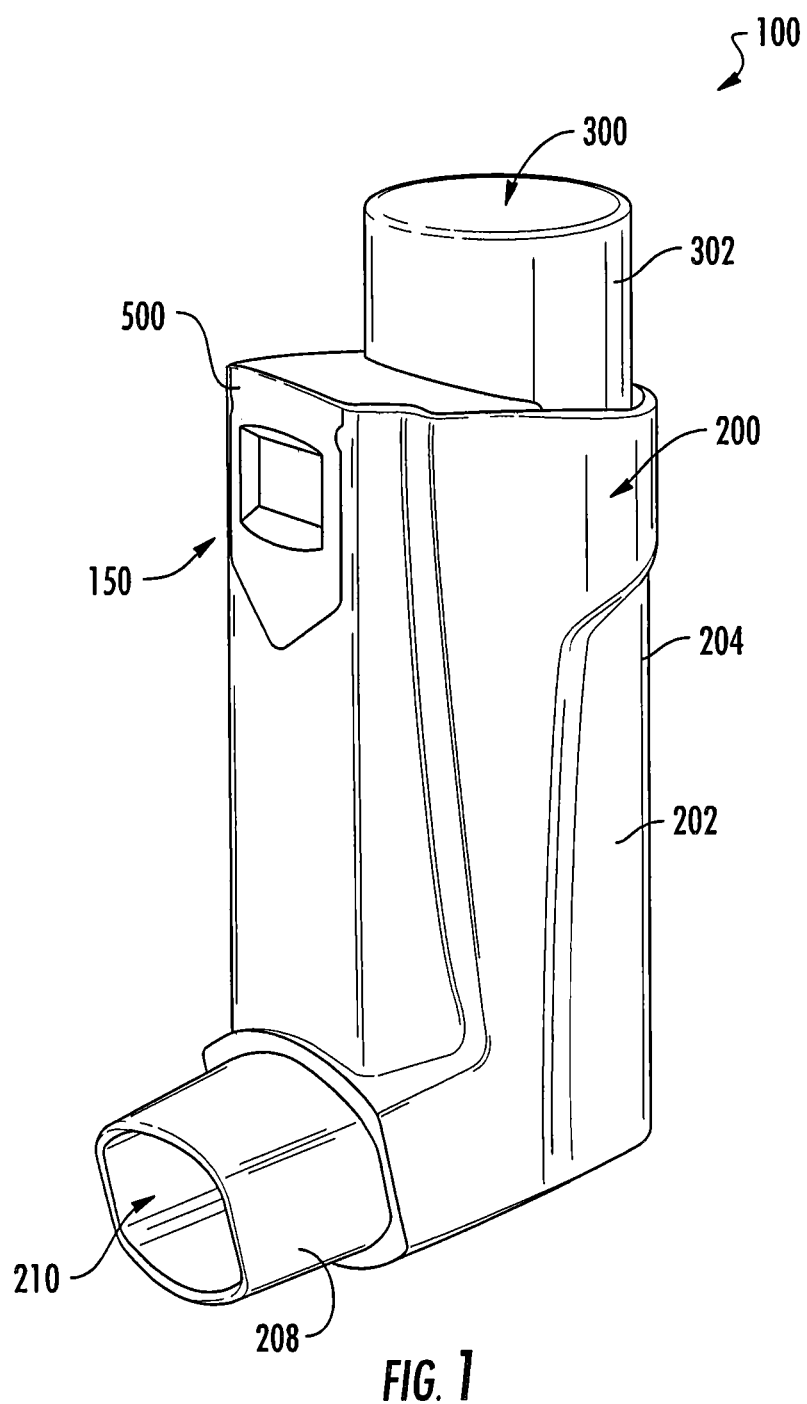
FIG. 1 is a perspective view of a metered-dose inhaler assembly according to some embodiments.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

Embodiments according to the present invention will now be described with reference to FIGS. 1-7 As illustrated, a metered-dose inhaler (MDI) 100 includes an actuator 200, a canister 300, and a dose counter 150 that includes a circuit assembly 400 and a triggering unit 500.

The actuator 200 includes a housing 202 that has a canister portion 204 with an opening 206 for receiving the canister 300 therein, and a dispensing portion 208 that includes an opening 210 for dispensing a metered amount of a pharmaceutical formulation. The actuator 200 further includes a bottom wall 212, a top opening 214 and a stem block 216. The canister 300 includes a can or vial 302 with a top end 304 and a bottom end 306. The canister 300 further includes a valve stem 308 at the bottom end 306.

When the canister 300 is positioned in the actuator 200, the MDI 100 is actuated when a user presses the vial top end 304 so that the valve stem 308 contacts the bottom wall 212 of the housing 202. The valve stem 308 is pressed in a direction toward the vial 302, which then dispenses a metered-dose of the pharmaceutical formulation. In particular, the actuator 200 includes an interior sleeve or stem block 216 (FIGS. 3-5) that cooperates with the valve stem 308 to guide the valve stem 308 into a depressed position. The pharmaceutical formation exits the actuator 200 via the opening 210, which is sized and configured so that a user can position the opening 210 in his or her mouth or through another drug delivery device to inhale the dispensed dose.

Figure 2:
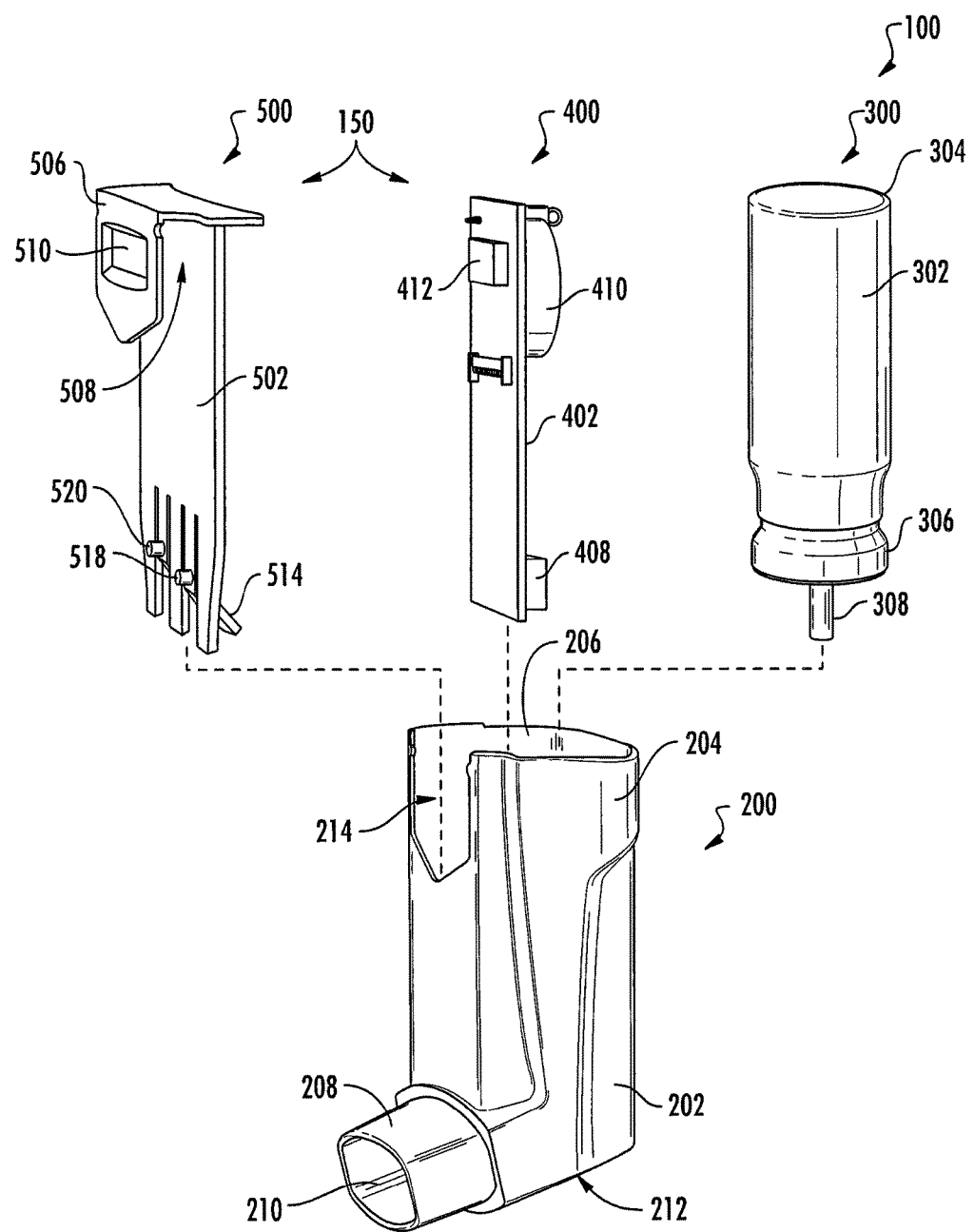
FIG. 2 is an exploded view of the metered-dose inhaler assembly of FIG. 1.
Figure 3:
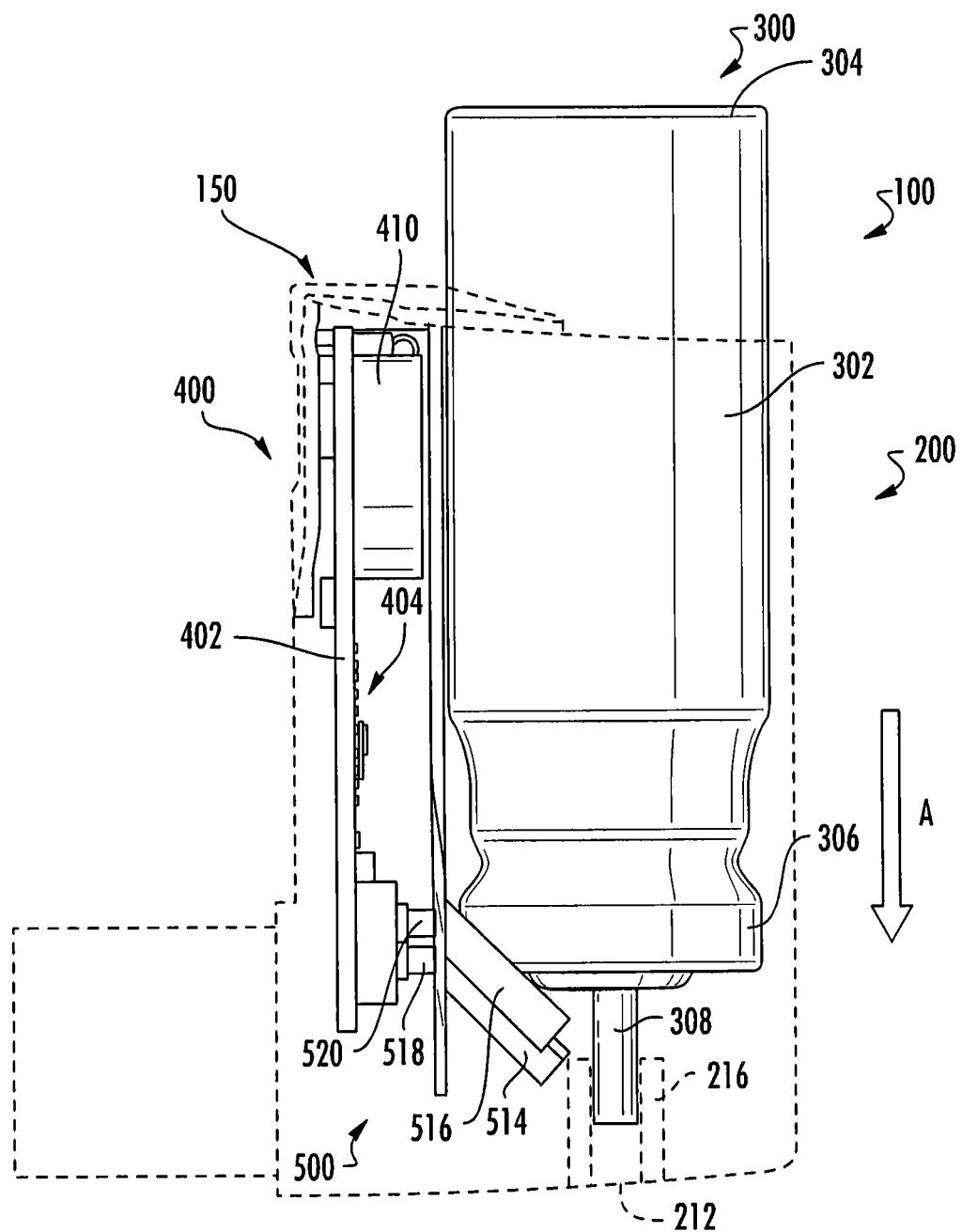
FIG. 3 is a side view of the canister and the dose counter, including a triggering unit and a circuit assembly, of the metered-dose inhaler assembly of FIG. 1 according to some embodiments in an at rest position.
Figure 4:
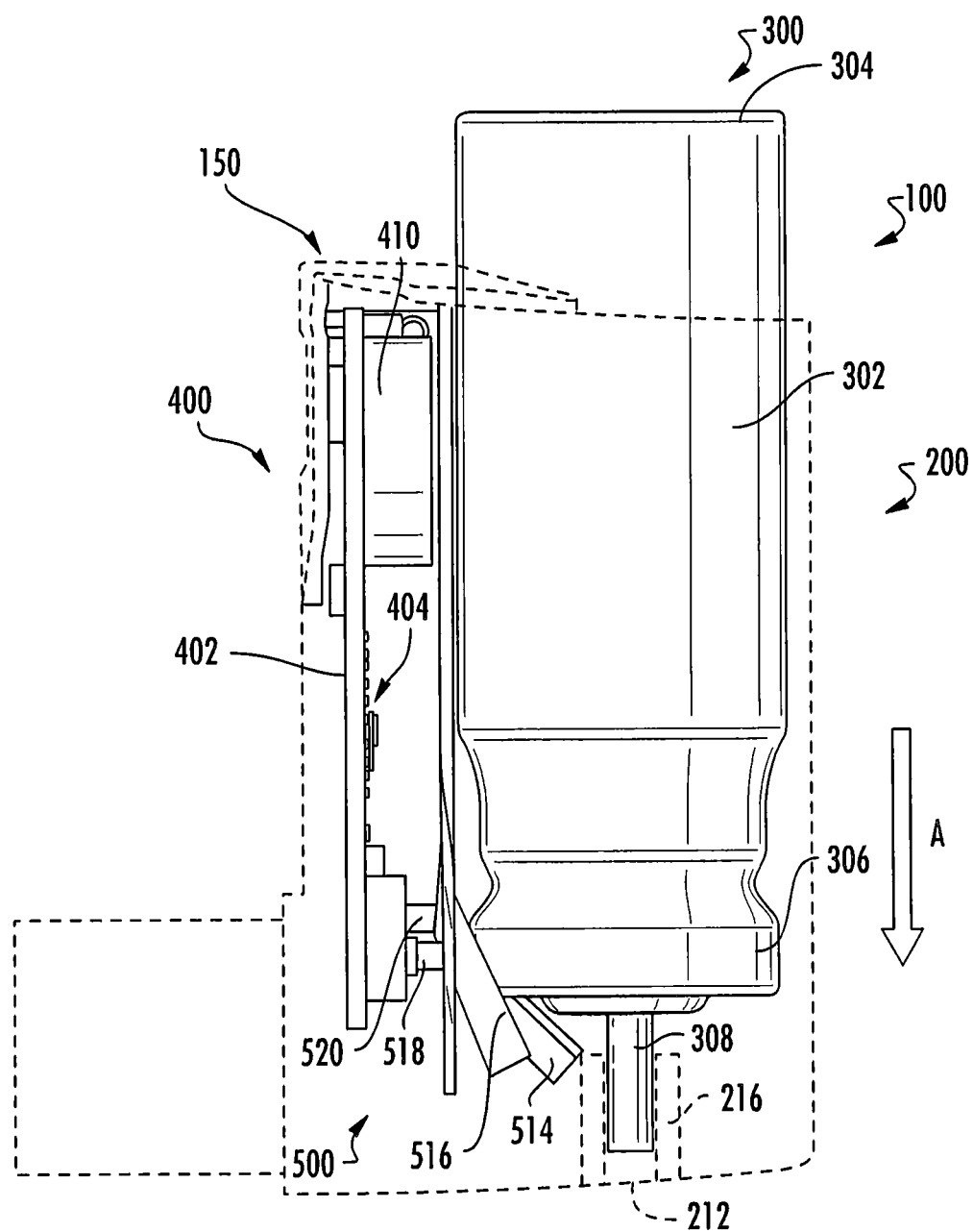
FIG. 4 is a side view of the canister and the dose counter, including a triggering unit and a circuit assembly, of the metered-dose inhaler assembly of FIG. 1 in an a partially-activated position.
Figure 5:
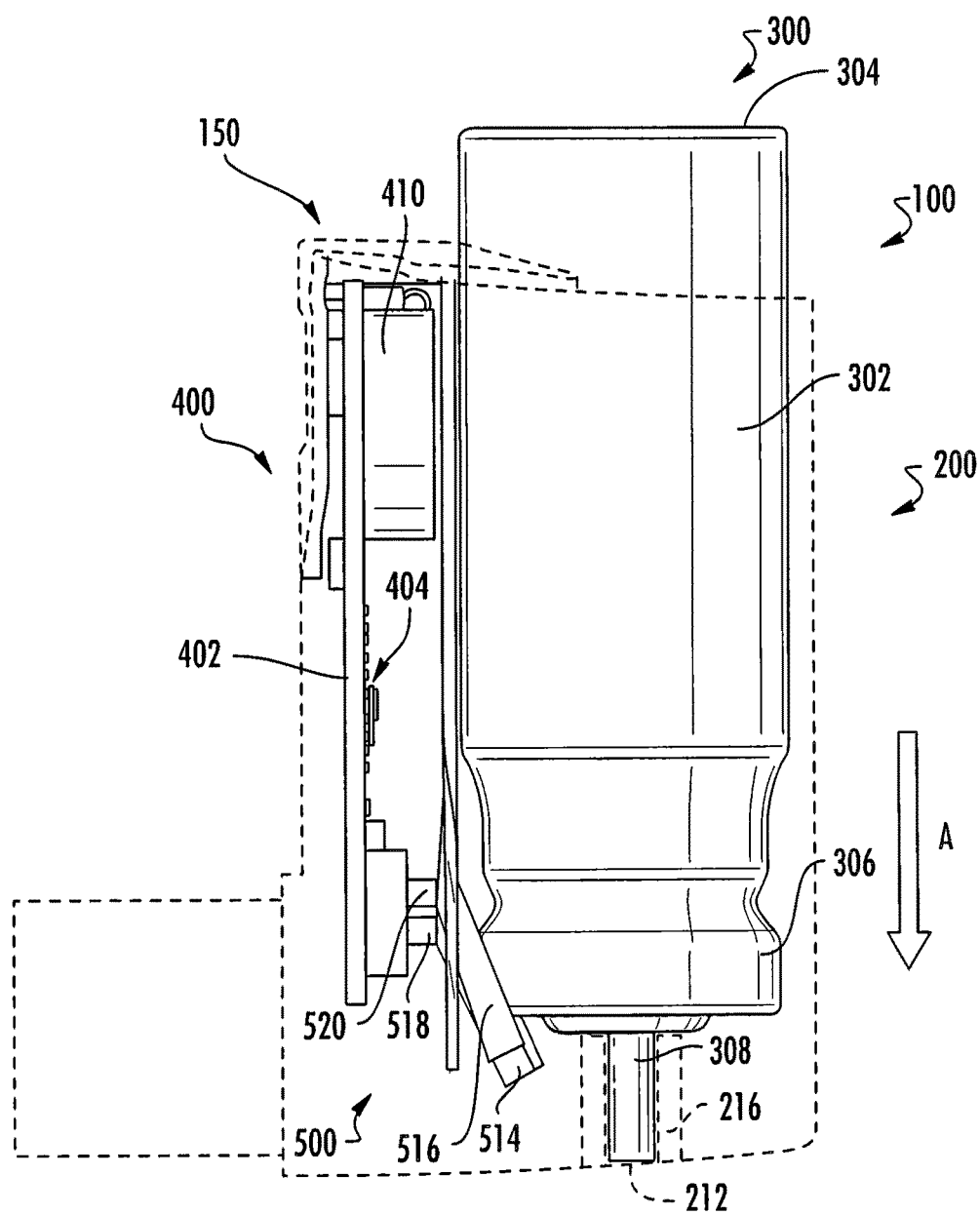
FIG. 5 is a side view of the canister and the dose counter, including a triggering unit and a circuit assembly, of the metered-dose inhaler assembly of FIG. 1 in a fully-activated position.
Figure 6A:
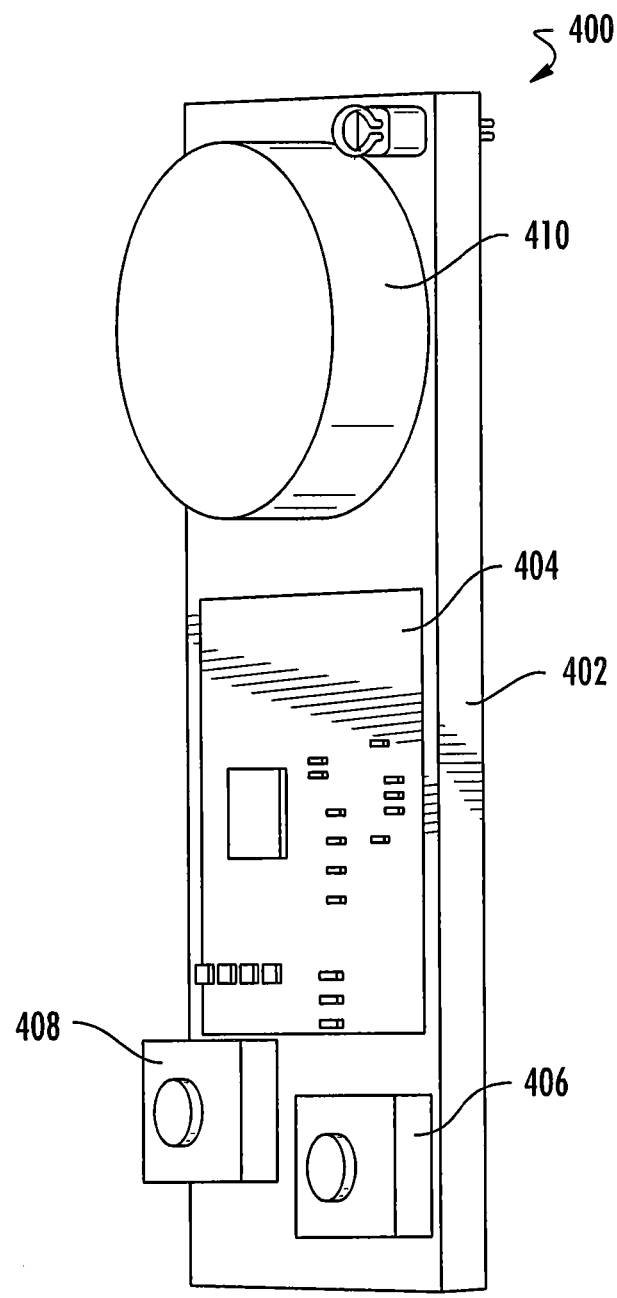
FIG. 6A is a side perspective view of a circuit assembly of the metered-dose inhaler assembly of FIG. 1.
Figure 6B:
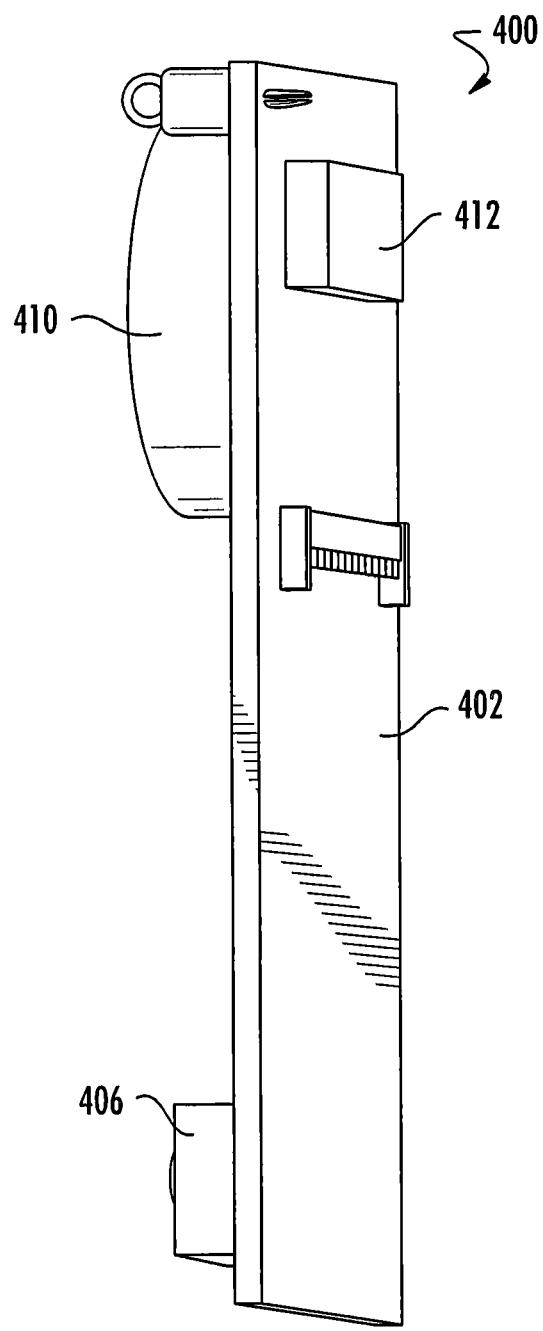
FIG. 6B is an opposing side perspective view of the circuit assembly of the metered-dose inhaler assembly of FIG. 1.
Figure 7:
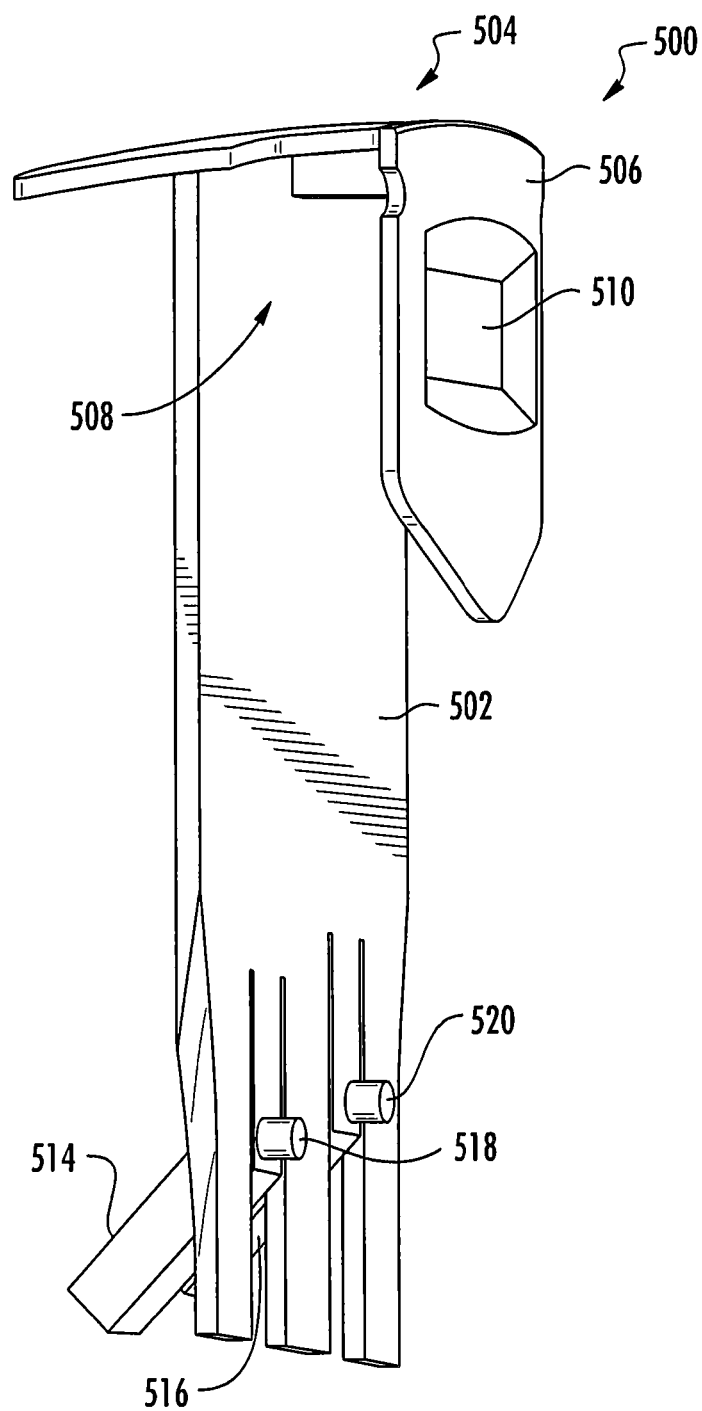
FIG. 7 is a perspective view of the triggering unit of the metered-dose inhaler assembly of FIG. 1.

As shown in FIG. 2 and FIGS. 6A-6B, the circuit assembly 400 includes a substrate 402 with a counting circuit 404, two spatially-offset switches 406, 408 and a battery 410 on one side (FIG. 6A), and a display 412 on an opposing side (FIG. 6B). As illustrated in FIGS. 2 and 7, the triggering unit 500 includes a body 502 with a top portion 504 and a bottom portion 512. The top portion 504 includes an overhanging portion 506 that forms an inverted U-shape and defines a recessed opening 508 and further includes a display opening 510. The bottom portion 512 includes at least two protruding finger members 514, 516 that are connected, respectively, to at least two trigger members 518, 520. As shown in FIGS. 1-5, the circuit assembly 400 is positioned in the recessed opening 508 of the triggering unit 500 so that the display 412 is visible to the user through the display opening 510 of the triggering unit 500. The circuit assembly 400 and the triggering unit 500 are positioned in the actuator 200 adjacent the canister 300 so that the protruding finger members 514, 516 of the triggering unit 500 are at the bottom end 306 of the vial 302 in an at rest position (FIG. 3).

As shown in FIG. 3, the trigger members 518, 520 are in a rest position in which the trigger members 518, 520 do not interact with or trigger the switches 406, 408 on the circuit assembly 400. When the canister 300 is moved in a longitudinal direction of arrow A as shown in FIG. 4, the canister bottom end 306 engages with the finger member 516 so that the trigger member 520 depresses and engages the switch 408. When the canister 300 moves a longitudinal distance as shown in FIG. 4, the finger member 516 is moved in a lateral direction by the canister 300 so that the trigger member 520 also moves in the lateral direction to depress the switch 408. When the canister 300 is moved an additional longitudinal distance in the direction of arrow A as shown in FIG. 5, the canister bottom end 306 engages with the other finger member 514 so that the finger member 514 moves in the lateral direction and the trigger member 518 depresses and engages the switch 406. As shown in FIG. 5, the valve stem 308 also contacts the bottom wall 212 of the housing 202 and dispenses the pharmaceutical formulation.

Accordingly, the trigger members 518, 520 are spatially offset in the longitudinal direction so that, when the canister 300 is actuated, the trigger member 520 triggers the switch 408 at a first time, and then the trigger member 518 triggers the switch 406 at a second time that is subsequent to the first time. The switches 406, 408 are likewise spatially offset to generally align with the trigger members 518, 520. Therefore, during actuation of the canister 300, the switches 406, 408 are activated successively at two different times based on the longitudinal offset between the trigger members 518, 520 and the switches 406, 408. The time difference between the activation of the switches 406, 408 may be used to determine whether sufficient force has been applied to the canister 300 to activate the valve 308. For example, if the time difference between the activation of the switches 406, 408 is too long, then the canister 300 is likely moving at a slow rate of speed when the valve 308 is depressed and may be unlikely to dispense a dose. If the time difference between the activation of the switches 406, 408 is sufficiently short, then the canister 300 is likely moving at a higher rate of speed so that when the valve 308 is depressed, full activation of the canister 300 and accurate dispensing of the pharmaceutical formulation is achieved.

Figure 8:
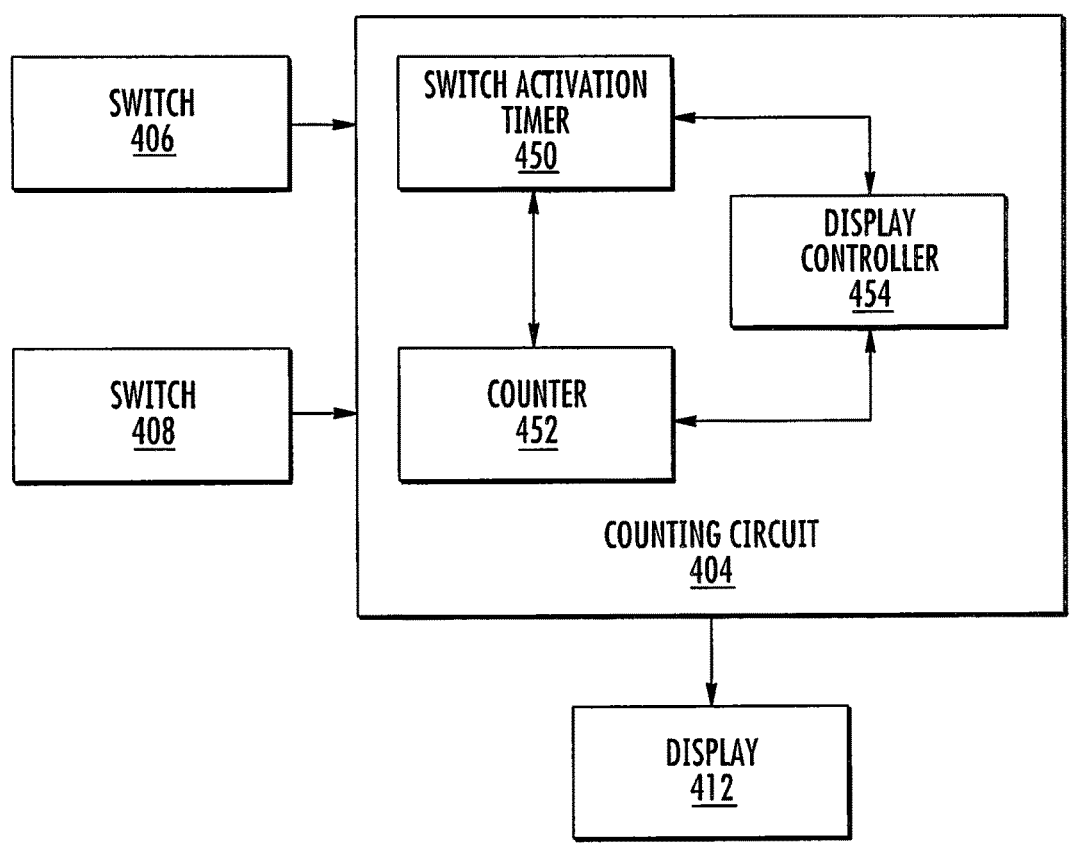
FIG. 8 is a schematic diagram of the switches, counting circuit and display of the circuit assembly of the metered-dose inhaler assembly of FIG. 1.
Figure 9:
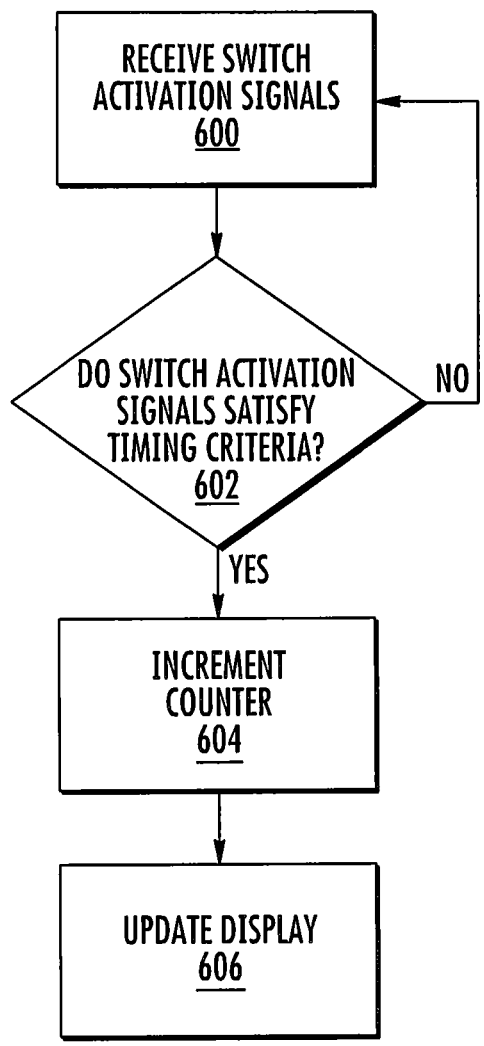
FIG. 9 is a flowchart of operations according to some embodiments.

As shown in FIG. 8, the activation times of the switches 406, 408 are received as inputs to the counting circuit 404. The counting circuit 404 further includes a switch activation timer 450, a counter 452 and a display controller 454. As illustrated in FIGS. 8-9, the switch activation timer 450 receives the switch activation signals (Block 600; FIG. 9) and determines whether the switch activation signals satisfy a timing criteria (Block 602). For example, the timing criteria can be a time difference that is less than a predetermined threshold amount that indicates a successful actuation of the canister 300. The threshold amount may be an experimentally determined amount of time that indicates, for example, that the speed at which the canister 300 is depressed is sufficient to actuate the valve 308. The timing criteria may also include confirming that both switches 406, 408 have been activated. If the timing criteria are met at Block 602, then the switch activation timer 450 increments counting indicia at the counter 452 to indicate that a dose has been dispensed (Block 604). The display controller 454 receives the counting information from the switch activation timer 450 and/or the counter 452 and updates the display 412 (Block 606). The counter 452 may increment counting indicia in either a positive or negative direction. For example, the display 412 may display a number of doses left in the canister 300 and decrease the counter 452 when the canister 300 is depressed and the valve 308 is activated, or the display 412 may display a number of doses that have been dispensed and increase the counter 452 when the valve 308 is activated. In addition, the display controller 454 may also control the display 412 to display other information, such as an expiration date of the medication, a number of prescription refills remaining for the prescription, a time of day or a time at which the last dose was administered, and/or a message to show whether there was a sufficient dose (e.g., an error message). In particular embodiments, the display 412 is an electronic ink display, such as an electrophoretic display (E Ink Corporation, Cambridge, Mass., USA), which may reduce power consumption.

In the position illustrated in FIG. 5, the valve stem 308 is generally at a fully depressed position such that the valve stem 308 is at the bottom wall 212 of the actuator 200 to dispense the pharmaceutical formulation provided that the valve stem 308 has been depressed with sufficient force and/or speed. Accordingly, the activation of the second switch 408 indicates that the valve stem 308 has reached the depressed position. In this configuration, the timing of the activation of the switches 406, 408 combined with the depressed position of the valve stem 308 indicated when the second switch 408 is activated may be used to determine whether the pharmaceutical formulation has been dispensed.

As illustrated in FIGS. 2-5, the body portion 502 of the triggering unit 500 is configured to be received in the actuator housing 202 between a wall of the housing 202 and the canister 300. The circuit assembly 400 may be positioned between the triggering unit body portion 502 and the wall of the actuation housing 202. In this configuration, the circuit assembly 400 and the triggering unit 500 may be positioned in the actuator 200 without generally requiring significant changes to the dimensions of the actuator 200 so that the look and feel of the actuator 200 is similar or identical to conventional actuator/canister assemblies. Accordingly, the circuit assembly 400 and the triggering unit 500 may be incorporated into the actuator 200 without substantially changing operation of the inhaler 100 by the user to potentially increase user acceptance and ease of use.

The finger members 514, 516 may be biased in a direction toward the canister 300 and move in a lateral direction toward the wall of the actuation housing 202 when the finger members 514, 516 are moved by movement of the canister 300 in the longitudinal direction. The finger members 514, 516 may automatically return to the position shown in FIG. 3 after actuation of the switches 406, 408.

Although embodiments according to the invention are described herein with respect to a dose counter 150 that includes the circuit assembly 400 and the triggering unit 500, it should be understood that various modifications of the dose counter 150 are within the scope of the invention. For example, the circuit assembly 400 and the triggering unit 500 may be rigidly connected to one another and/or provided as a single unit.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A dose counter for a metered dose inhaler, the metered dose inhaler having an actuation housing and canister with an activation valve at a valve end of the canister, the canister being configured to be received in the actuation housing and to move from a rest position to an activation position in which the valve is depressed against a bottom portion of the actuation housing, the dose counter comprising:
a triggering unit having at least a first and a second trigger member thereon, the triggering unit being configured to interact with the canister when the canister moves in a longitudinal direction from the rest position to the activation position;
a circuit assembly having a substrate with at least a first and a second switch thereon, the first and second switches being configured to interact with the first and second trigger members when the canister moves from the rest position to the activation position such that the first trigger member triggers the first switch when the canister reaches a first longitudinal position and the second trigger member triggers the second switch when the canister reaches a second longitudinal position that is different from the first longitudinal position during movement of the canister from the rest position to the activation position;
wherein the first and second trigger members are configured to move from a first position to a second position to activate the first and second switches when the canister moves in the longitudinal direction;
and the circuit assembly further comprises a counting circuit that is configured to receive a signal from the first and second switches indicating at least a first time when the first switch is triggered by the first trigger member and a second time when the second switch is triggered by the second trigger member, and to determine when the metered dose inhaler is activated responsive to the first and second time, wherein the counting circuit is configured to determine whether the metered dose inhaler is activated when a time difference between the first and second time is less than a threshold amount.

2. The dose counter of claim 1, wherein the first and second trigger members are configured to move from a first position to a second position to activate the first and second switches when the canister moves in the longitudinal direction.

3. The dose counter of claim 2, wherein the triggering unit comprises first and second finger members that are operatively connected to the first and second trigger members, respectively, wherein the first finger member is configured to move the first trigger member in a lateral direction when the canister reaches the first longitudinal position and the second finger member is configured to move the second trigger member in the lateral direction when the canister reaches the second longitudinal position.

4. The dose counter of claim 3, wherein the second longitudinal position of the canister is a position in which the valve is depressed against the bottom portion of the actuation housing.

5. The dose counter of claim 4, wherein when the triggering unit is positioned in the actuation housing between the wall of the actuation housing and the canister, first and second finger members extend in a direction toward the canister in the first position and move in a lateral direction toward the wall of the actuation housing in the second position.

6. The dose counter of claim 1, wherein the triggering unit comprises a body portion that is configured to be positioned in the actuation housing between a wall of the actuation housing and the canister.

7. The dose counter of claim 6, wherein when the triggering unit is positioned in the actuation housing between the wall of the actuation housing and the canister, the first and second finger members extend in a direction toward the canister in the first position and move in a lateral direction toward the wall of the actuation housing in the second position.

8. The dose counter of claim 7, wherein the first and second finger members of the triggering unit are biased to the first position when the canister is in the rest position.

9. The dose counter of claim 7, wherein the triggering unit body portion has a first end and an opposite second end, wherein the finger members are on the first end and the triggering unit further comprises an overhanging member that defines a recessed opening that is configured to receive the counting circuit assembly therein.

10. The dose counter of claim 9, wherein the overhanging member further comprises a display opening for receiving the display therein so that the display is visible to a user.

11. The dose counter of claim 6, wherein the circuit assembly is configured to be positioned between the triggering unit body portion and the wall of the actuation housing.

12. The dose counter of claim 11, wherein the first and second switches are on a first side of the circuit assembly substrate, and the circuit assembly further comprises a display on a second, opposite side of the circuit assembly substrate.

13. The dose counter of claim 12, wherein when the counting circuit determines when the metered dose inhaler is activated responsive to the first and second time, the counting circuit increments a counting indicia, and displays the counting indicia on the display.

14. The dose counter of claim 12, wherein the display is an electronic ink display.

15. The dose counter of claim 1, wherein the counting circuit is positioned on the substrate of the circuit assembly.

16. A metered-dose inhaler assembly comprising:
   a metered dose inhaler having an actuation housing and canister with an activation valve at a valve end of the canister, the canister being configured to be received in the actuation housing and to move from a rest position to an activation position in which the valve is depressed against a bottom portion of the actuation housing;
   a dose counter in the actuation housing, the dose counter comprising:
      a triggering unit having at least a first and a second trigger member thereon, the triggering unit being configured interact with the canister when the canister moves in a longitudinal direction from the rest position to the activation position;
      a circuit assembly having a substrate with at least a first and a second switch thereon, the first and second switches being configured to interact with the first and second trigger members when the canister moves from the rest position to the activation position such that the first trigger member triggers the first switch when the canister reaches a first longitudinal position and the second trigger member triggers the second switch when the canister reaches a second longitudinal position that is different from the first longitudinal position during movement of the canister from the rest position to the activation position; and
      a counting circuit that is configured to receive a signal from the first and second switches indicating at least a first time when the first switch is triggered by the first trigger member and a second time when the second switch is triggered by the second trigger member, and to determine when the metered dose inhaler is activated responsive to the first and second time.

17. The metered-dose inhaler assembly of claim 16, wherein the first and second trigger members are configured to move from a first position to a second position to activate the first and second switches when the canister moves in the longitudinal direction.

18. The metered-dose inhaler assembly of claim 17, wherein the triggering unit comprises first and second finger members that are operatively connected to the first and second trigger members, respectively, wherein the first finger member is configured to move the first trigger member in a lateral direction when the canister reaches the first longitudinal position and the second finger member is configured to move the second trigger member in the lateral direction when the canister reaches the second longitudinal position.

19. The metered-dose inhaler assembly of claim 18, wherein the second longitudinal position of the canister is a position in which the valve is depressed against the bottom portion of the actuation housing.

20. The metered-dose inhaler assembly of claim 16, wherein the counting circuit is configured to determine whether the metered dose inhaler is activated when a time difference between the first and second time is less than a threshold amount.

21. The metered-dose inhaler assembly of claim 16, wherein the triggering unit comprises a body portion that is configured to be positioned in the actuation housing between a wall of the actuation housing and the canister.

22. The metered-dose inhaler assembly of claim 21, wherein when the triggering unit is positioned in the actuation housing between the wall of the actuation housing and the canister, the first and second finger members extend in a direction toward the canister in the first position and move in a lateral direction toward the wall of the actuation housing in the second position.

* * * * *

UNITED STATES PATENT AND TRADEMARK OFFICE
CERTIFICATE OF CORRECTION

PATENT NO. : 9,943,656 B2
APPLICATION NO. : 15/311098
DATED : April 17, 2018
INVENTOR(S) : Shears et al.

Page 1 of 1

It is certified that error appears in the above-identified patent and that said Letters Patent is hereby corrected as shown below:

On the Title Page

Item (71) Applicant should read -- PRESSPART GMBH & CO. KG, Marsberg (DE) --

Signed and Sealed this
Twentieth Day of November, 2018

Andrei Iancu
*Director of the United States Patent and Trademark Office*